United States Patent
Rudloff

(10) Patent No.: US 7,303,139 B1
(45) Date of Patent: Dec. 4, 2007

(54) SYSTEM AND METHOD FOR IDENTIFYING AND AUTHENTICATING ACCESSORIES, AUXILIARY AGENTS AND/OR FUELS FOR TECHNICAL APPARATUS

(75) Inventor: Peter Rudloff, Ladenburg (DE)

(73) Assignee: Kabushiki Kaisha Hitachi Seisakusho (Hitachi, Ltd.), Tokyo (JP)

( * ) Notice: Subject to any disclaimer, the term of this patent is extended or adjusted under 35 U.S.C. 154(b) by 0 days.

(21) Appl. No.: 09/403,174

(22) PCT Filed: Feb. 19, 1999

(86) PCT No.: PCT/EP99/01091

§ 371 (c)(1),
(2), (4) Date: Oct. 18, 1999

(87) PCT Pub. No.: WO97/11790

PCT Pub. Date: Apr. 3, 1997

(30) Foreign Application Priority Data

Feb. 20, 1998 (DE) ............................ 198 07 177
May 20, 1998 (DE) ............................ 198 22 751

(51) Int. Cl.
*G06K 19/06* (2006.01)
(52) U.S. Cl. ...................... 235/494; 235/375
(58) Field of Classification Search ................ 235/494, 235/375, 454, 462.04, 462.07
See application file for complete search history.

(56) References Cited

U.S. PATENT DOCUMENTS 4,844,509 A   7/1989  Kasprzak et al. ...... 235/462.04
4,949,381 A   8/1990  Pastor ........................... 380/51
5,307,423 A * 4/1994  Gupta et al.
5,422,470 A * 6/1995  Kubo .................... 235/462.09

(Continued)

FOREIGN PATENT DOCUMENTS

DE          29702805 U1    5/1997

(Continued)

OTHER PUBLICATIONS

Doermann, D., et al., "Applying algebraic and differential invariants for logo recognition" in: *Machine Vision and Applications* (1996) 9:73-86.

*Primary Examiner*—Daniel St.Cyr
(74) *Attorney, Agent, or Firm*—Townsend and Townsend and Crew LLP

(57) ABSTRACT

In the case of a system for identifying and authenticating accessories, auxiliary substances and/or operating substances for items of equipment, the accessories or the auxiliary or operating substances or their storage containers are provided with a data carrier portion on which information that can be detected by the human eye and is distinctive to a human viewer is stored. The item of equipment is in this case provided with a reading and evaluating device for this information. The reading and evaluating device has a comparison device for comparing the read information with a stored item of information as well as an enabling controller for at least one functional component of the item of equipment. If the read information coincides with the stored information an authenticating signal or enabling signal is supplied by the enabling controller to the functional component, which thereupon permits operation of the item of equipment and if the read information does not coincide with the stored information disables operation of the item of equipment and emits a warning signal.

11 Claims, 2 Drawing Sheets

U.S. PATENT DOCUMENTS

| | | | |
|---|---|---|---|
| 5,548,110 A * | 8/1996 | Storch et al. | |
| 5,617,481 A * | 4/1997 | Nakamura | 382/101 |
| 5,770,841 A * | 6/1998 | Moed et al. | |
| 5,917,925 A * | 6/1999 | Moore | 382/101 |
| 6,041,704 A * | 3/2000 | Pauschinger | 101/91 |

FOREIGN PATENT DOCUMENTS

| | | |
|---|---|---|
| DE | 19612406 A1 | 10/1997 |
| EP | 733991 A2 * | 9/1996 |
| EP | 782053 A2 * | 7/1997 |

* cited by examiner

SYSTEM AND METHOD FOR IDENTIFYING AND AUTHENTICATING ACCESSORIES, AUXILIARY AGENTS AND/OR FUELS FOR TECHNICAL APPARATUS

BACKGROUND OF THE INVENTION

The invention relates to a system for identifying and authenticating accessories, auxiliary and/or operating substances for items of equipment. It further relates to a method for detecting and decoding information stored on an optically readable data carrier portion.

It is often the case that accessory parts or auxiliary substances or operating substances for items of equipment are produced and distributed not only by the manufacturer of the item of equipment but also by third-party suppliers. Such products from third-party suppliers often do not meet the high quality and safety requirements of the manufacturer of the item of equipment but can be used in conjunction with the item of equipment without major technical problems. For the manufacturer of an item of equipment, it is generally difficult to ensure the reliability and safety of the equipment if such accessory products or auxiliary or operating substances from third-party suppliers are used, since the decision on the use of such third-party supplier products generally lies with the user of the equipment.

It is therefore not only in the interest of the equipment manufacturer but also in the interest of the users of such equipment if it can be reliably ensured that equipment can be used only with accessories authorized by the equipment manufacturer and with auxiliary or operating substances authorized by the equipment manufacturer.

SUMMARY OF THE INVENTION

It is therefore an object of the present invention to provide a marking for accessories and auxiliary or operating substances or their storage containers as well as an identification system which allow a clear identification or authorization by the manufacturer of an item of the equipment and which allow the proliferation of unauthorized accessories or unauthorized auxiliary or operating substances to be prevented.

The provision of the information that can be detected by the human eye and is distinctive to a human viewer on the accessories or the auxiliary or operating substances or their storage containers and of the reading and evaluating device for this information on the item of equipment makes it possible for the equipment to inspect, preferably likewise visually, whether the information provided on the data carrier portion coincides with a prescribed item of information stored in the equipment, so that operation of an item of equipment is made possible only if they coincide. This authentication function of the system according to the invention is supplemented by the detectability of information by the human eye and by its property of being distinctive to a human viewer, generally directly, that is to say without prolonged viewing. Consequently, the user can initially check with his own eyes whether the accessories or auxiliary or operating substances are products authorized by the manufacturer.

It is advantageous in particular if the information that can be detected by the human eye and is distinctive to the human viewer is formed by a trademark. If use of the item of equipment with the accessories or the auxiliary or operating substances is in this case only authorized if the trademark detectable by the human eye, generally a registered and protected mark of the manufacturer, is provided on the data carrier portion, the manufacturer can prevent the distribution of unauthorized accessories or unauthorized auxiliary or operating substances for the item of equipment directly on the basis of a trademark infringement, since an unauthorized third-party manufacturer must use the otherwise protected trademark in an unallowed way to ensure operability. Instead of a trademark, an otherwise protected graphic or typographic element may also be provided.

If the data carrier portion has a first region, in which only machine-readable information is stored, and a second region, in which the information that can be detected by the human eye and is distinctive to the human viewer is stored, it is possible to provide on the data carrier portion, in addition to the information that can be detected by the human eye, data which can likewise be read and evaluated by the reading and evaluating device of the item of equipment, this data having for example technical data of the product, in other words of the corresponding accessories or of the corresponding auxiliary or operating substance. In this case, the first region may contain a variable, product-dependent item of information, while the second region comprises a static manufacturer-dependent item of information, which is the same for all products.

It is preferable if at least one reference marking for the orientation of the reading device is provided on the data carrier portion. As a result, reliable detection of the data on the data carrier portion is ensured, even if the data carrier portion is moved past the reading device in different positions.

It is also preferable if the information stored on the first region of the data carrier portion is formed by a machine-readable code and the information stored on the second region of the data carrier portion is formed by a trademark.

In a further preferred embodiment, the first region of the data carrier portion has a multiplicity of lines of a binary pixel code, the binary pixel code containing a plurality of lines of the only machine-readable information, and the second region of the data carrier portion has a plurality of lines of a pixel code which together form the information that can be detected by the human eye and is distinctive to the human viewer.

The line-by-line binary pixel code in the first region provides a coding capability which allows a very high data density per unit area of the data carrier portion.

The representation of the information that can be detected by the human eye and is distinctive to the human viewer as a line-by-line pixel code facilitates the evaluation of the information of the data carrier portion, which in this way can be performed with one and the same reading and evaluating device for the first region and the second region.

It is preferred if a machine-readable limit marking, which preferably comprises at least one blank line, is provided between the first region of the data carrier portion and the second region of the data carrier portion. This provides a clear delimitation of the first region and second region both for the human eye and for the reading device.

It is also preferred if the reference marking has a frame reaching around at least one of the two regions of the data carrier portion.

To facilitate reading out, the binary pixel code of a line has in each case a row of adjacently lying bit markings of the binary representation of an item of information.

It is preferred if, to increase reading-out reliability, binary bit markings for a check digit for the binary representation of the information are additionally provided in each line.

A method for detecting and decoding information provided on an optically readable data carrier portion of a system which is detectable by the human eye and distinctive to a human viewer, comprises the steps: registering the optical information present on the data carrier portion, reading out the optical information present on the data carrier portion, comparing the read-out information with a stored information sample and generating an authenticating signal if the read-out information of the second region has been detected as coinciding with the stored information sample.

An alternative method for detecting and decoding information provided on an optically readable data carrier portion, with at least part of the information being detectable by the human eye and distinctive to a human viewer, comprises: registering the optical information present on the data carrier portion, preferably identifying the reference marking, identifying the first and second regions of the data carrier portion, reading out and decoding the binary information contained in the first region, reading out the information contained in the second region, comparing the read-out information of the second region with a stored information sample and generating an authenticating signal if the read-out information of the second region has been detected as coinciding with the stored information sample.

The invention is explained in more detail below on the basis of an example with reference to the drawings.

DESCRIPTION OF THE PREFERRED EMBODIMENTS

Figure 1:
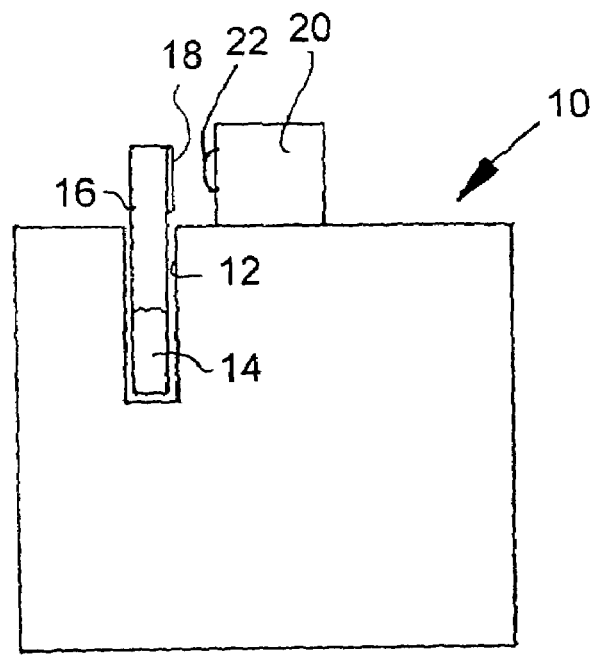
FIG. 1 shows the schematic structure of a system according to the invention.

FIG. 1 is a schematic representation of an item of equipment 10, which has a receptacle 12 for a storage container 16 containing an auxiliary substance 14. The item of equipment is, for example, an analyzer for the automatic analysis of chemical or biological specimens, the auxiliary substance being formed by a reagent which is used for the analysis of a specific specimen (not shown) in the item of equipment 10.

The storage container 16 is provided in its upper region with a data carrier portion 18, which is explained in further detail below with reference to FIG. 2. Provided on the item of equipment 10 is a reading and evaluating device 20, which has for example a video camera or a fixed video camera, the lens 22 of which is directed at the data carrier portion 18.

Figure 2:
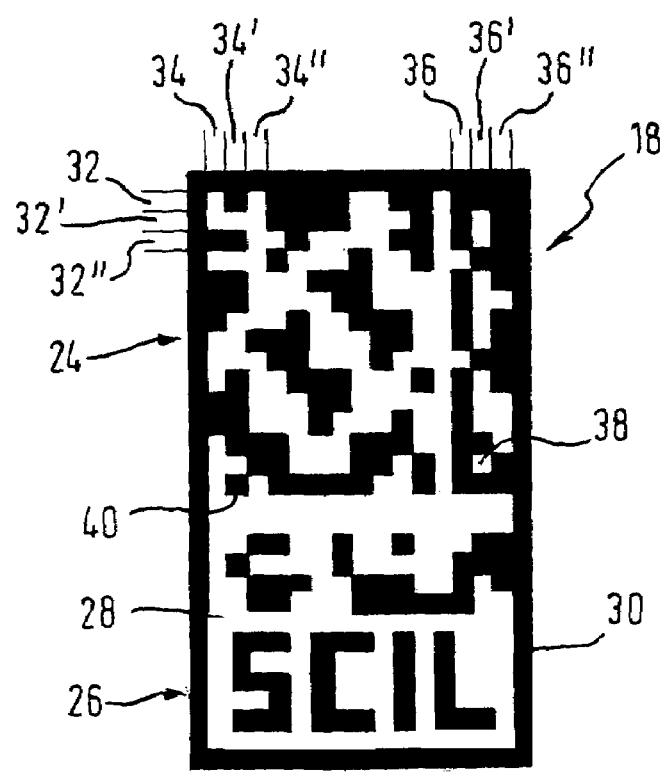
FIG. 2 shows a data carrier portion of a system according to the invention.

In FIG. 2, the data carrier portion 18 is reproduced in a greatly enlarged form. The data carrier portion 18 has a first region 24, in which a machine-readable item of information is stored. Furthermore, the data carrier portion 18 has a second region 26, in which an item of information that can be detected by the human eye and is distinctive to the human viewer is stored. In the example of FIG. 2, this is the sequence of letters "SCIL".

Provided as a limit marking 28 between the first region and the second region is a blank line, in which no binary information is stored. The first region 24 and the second region 26 as well as the limit marking 28 are together surrounded by a frame forming a reference marking 30.

The first region 24 comprises a multiplicity of lines, 32, 32', 32" of a binary pixel code, which has a multiplicity of columns 34, 34', 34" per line, each combination of line and column representing a pixel location which, either by a white pixel or a black pixel, contains an item of binary optical information. Provided at the right-hand end of the lines are three columns 36, 36', 36", which, in each case in combination with a line, contain a binary code of a check digit for the respective line.

In the present example, a white bit marking 38 denotes the binary value "0", whereas a black bit marking 40 denotes the binary value "1".

In the second region 26, the letters "SCIL" are formed by corresponding line-by-line binary markings, the totality of the lines in the second region 26 forming a combination of letters "SCIL" that can be detected by the human eye and that is distinctive to a human viewer. Instead of letters, a graphic representation, for example a logo, may be depicted equally well in the second region.

If during operation the data carrier portion 18 is registered by the camera of the reading and evaluating device 20, firstly the region of the data carrier portion bearing the information is identified on the basis of the reference marking. Then, the image produced by the camera is analyzed line by line, in order to establish whether a light or dark or colored bit marking is present at a corresponding pixel location (combination of line and column), it being possible for different colored bit markings to be provided to increase the information density. The line-by-line coding in the first region 24 is decoded according to a prescribed coding algorithm and the second region 26 is identified on the basis of the limit marking 28. The depiction of the second region 26 is compared with a depiction stored in a memory of the item of equipment 10, whereupon, if the comparison shows identity of the stored depiction with the registered depiction of the data carrier 18, an authenticating signal is generated in the item of equipment 10, which in the present example allows the auxiliary substance 14 for the carrying out of an analysis and consequently makes the analysis possible. If, on account of a lack of coincidence, no authenticating signal is generated, an error message is issued on the item of equipment 10 and its operation is inhibited for the auxiliary substance 14.

Figure 3:
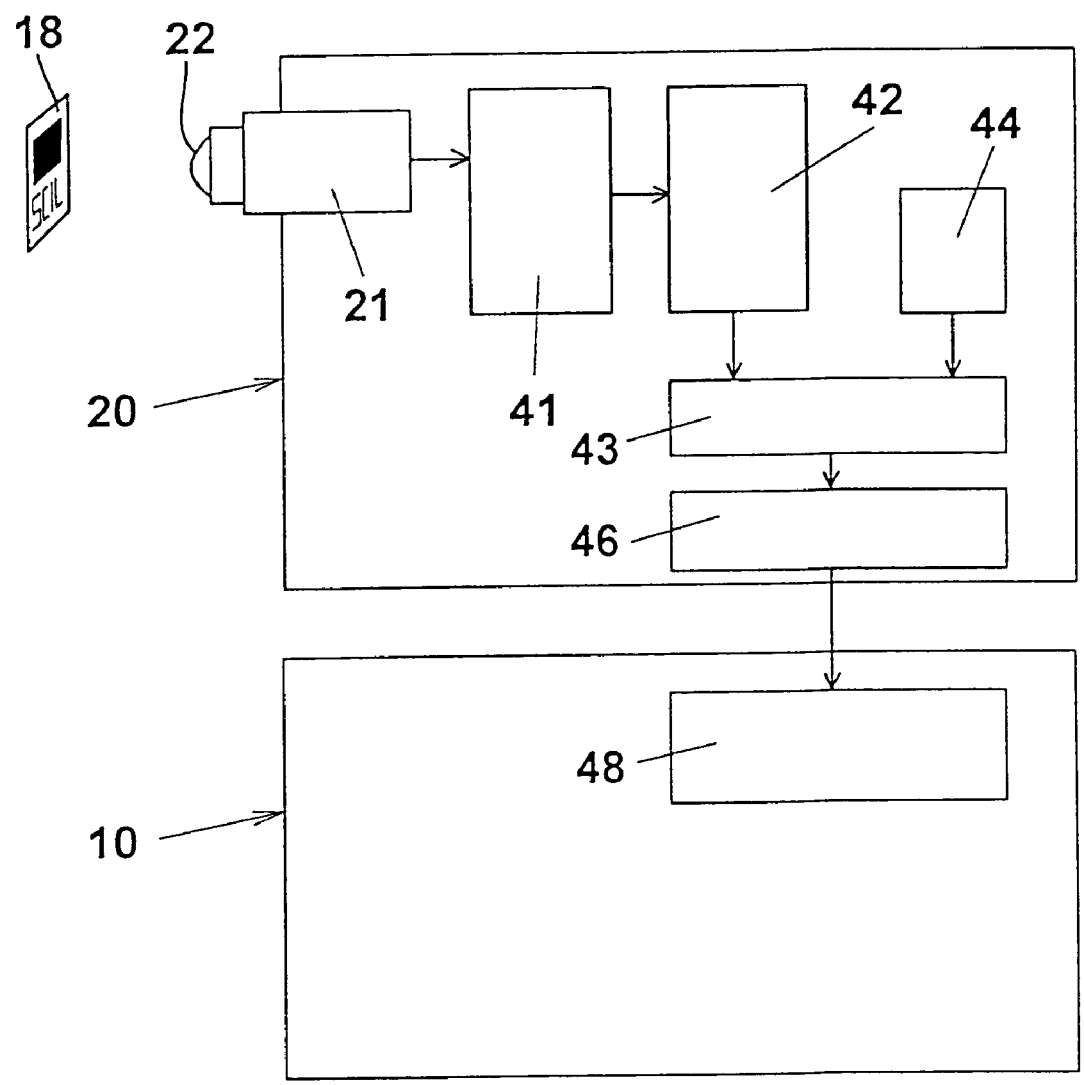
FIG. 3 shows a block diagram of the system according to the invention.

Represented in FIG. 3 is a block diagram which shows the basic structure of the system according to the invention for identification and authentication. The optical signal picked up by the lens 22 of the camera 21 from the data carrier portion 18 is converted in the camera 21 into an electronic image signal in a conventional way. The electronic image signal is read out, for example line by line, in a reading-out device 41 and decoded in a downstream decoding device 42, using a prescribed decoding algorithm. The information thus obtained is passed on to a comparison device 43, in which this information read out from the data carrier portion 18 is compared with an item of information stored in a memory device 44.

If the read information coincides with the stored information, an enabling signal is sent from the comparison device 43 to an enabling controller 46, which thereupon enables a functional component 48 of the item of equipment 10, so that the item of equipment 10 is ready to operate.

If the comparison of the read information and the stored information in the comparison device 43 does not lead to coincidence of the two items of information, a blocking signal is sent from the comparison device 43 to the enabling controller 46, which thereupon disables the functional component 48 of the item of equipment, so that the equipment is not ready to operate, and an optical and/or acoustic signal is triggered in order to indicate to the operator of the item of equipment 10 the lack of operational readiness of the equipment.

The functional component 48 may be, for example, a power supply or an open-loop and/or closed-loop control device for the item of equipment 10 or for part of the item of equipment 10.

The invention is not restricted to the above exemplary embodiment, which merely serves for a general explanation of the essential idea of the invention. Rather, the device according to the invention can, within the extent of protection, also assume configurations other than those described above. The device may in this case have in particular features which represent a combination of the respective individual features of the claims.

For example, a mirror-reflex camera or a video camera can also be equipped with a reading and evaluating device according to the invention, and the interchangeable lenses for this camera could be provided with a data carrier portion according to the invention, in order to permit only the use of original lenses of the camera manufacturer on this camera.

Reference numerals in the claims, the description and the drawings serve merely for better understanding of the invention and are not intended to restrict the extent of protection.

The invention claimed is:

1. A system for controlling the operation of an item of equipment by identifying and authenticating a substance handled by the item of equipment, the system comprising first machine-readable information concerning the substance and second information that can be detected by a human eye and is distinctive to a human viewer, the first and second informations being applied to the substance or to the container for the substance, a reading device adapted to read the first information and the second information, a memory storing authorizing information for the substance, and an evaluating device for comparing read second information with the authorizing information stored in the memory, the evaluating device enabling the operation of the item of equipment when the read second information coincides with the stored authorizing information by generating an enabling signal permitting operation of the item of equipment, and not enabling the operation of the item of equipment when the read second information does not coincide with the stored authorizing information.

2. A system according to claim 1, wherein
the substance or its storage container includes a data carrier portion where the second information is stored, and wherein
the evaluating device comprises
a comparator for comparing the read second information with the stored authorizing information, and
an enabling controller for at least one functional component of the item of equipment.

3. A system according to claim 2, including at least one reference making at the data carrier portion for orienting the reading device.

4. A system according to claim 3, wherein the reference marking has a frame extending around at least one of the first and second regions of the data carrier portion.

5. A system according to claim 2, wherein the data carrier portion has a first region where only the first information is stored, and a second region where the second information is stored.

6. A system according to claim 5, wherein
the first information stored at the first region of the data carrier portion is formed by a machine-readable code, and
wherein the second information stored at the second region of the data carrier portion is formed by a trademark.

7. A system according to claim 5, wherein
the first region of the data carrier portion has a multiplicity of lines of a binary pixel code, the binary pixel code containing the first machine-readable information, and
wherein the second region of the data carrier portion has a plurality of lines of a pixel code which together form the second information.

8. A system according to claim 7, wherein the binary pixel code of at least one of the lines has a row of adjacently lying bit markings of a binary representation of an item of information.

9. A system according to claim 8, including binary bit markings for a check digit for the binary representation of the information in each line.

10. A system according to claim 5, including a machine-readable limit marking comprising at least one blank line provided between the first region of the data carrier portion and the second region of the data carrier portion.

11. A method for controlling the operation of an item of equipment that handles a substance comprising applying first information which is dependent on the substance and is machine-readable to a first region associated with the substance, applying second information which is detectable by a human eye and distinctive to a human viewer to a second region associated with a substance, storing an information sample which corresponds to the second information, reading and decoding the machine-readable first information present at the first region, reading the second information present at the second region, comparing the read second information of the second region with the stored information sample, generating a signal when the read second information coincides with the stored information sample which permits operation of the item f equipment, and preventing the operation of the item of equipment when the read second information does not coincide with the stored information sample.

* * * * *